US005957955A

United States Patent [19]

Thomas

[11] Patent Number: 5,957,955

[45] Date of Patent: Sep. 28, 1999

[54] BACK STRETCHING SYSTEM

[76] Inventor: James Thomas, 10915 Julius St., Oakland, Calif. 94605-5235

[21] Appl. No.: 09/004,080

[22] Filed: Jan. 8, 1998

[51] Int. Cl.$^{6}$ .......... A61F 5/00

[52] U.S. Cl. .......... 606/243; 482/142; 482/907; 601/24; 602/32

[58] Field of Search .......... 606/241–244; 482/95, 96, 101, 907, 142–145; 602/32; 601/24

[56] References Cited

U.S. PATENT DOCUMENTS

| | | | |
|---|---|---|---|
| 1,456,317 | 5/1923 | Lauer | 482/145 |
| 1,911,572 | 5/1933 | Hulander et al. | 482/142 |
| 2,738,975 | 3/1956 | Zaboy | 482/145 |
| 2,774,349 | 12/1956 | Judavich | 606/243 |
| 2,783,045 | 2/1957 | Bosch | 482/96 |
| 3,741,200 | 6/1973 | Morin | 606/244 |
| 3,993,051 | 11/1976 | Maruyama | 606/242 |
| 4,333,644 | 6/1982 | Lambert, Jr. et al. | 482/101 |
| 4,627,422 | 12/1986 | Bates | 606/244 |
| 4,802,465 | 2/1989 | Slagle | 606/244 |
| 4,867,143 | 9/1989 | Morin | 606/244 |
| 4,890,604 | 1/1990 | Nelson | 602/32 |
| 5,108,354 | 4/1992 | Becker | 482/104 |

*Primary Examiner*—Richard J. Apley
*Assistant Examiner*—Victor K. Hwang

[57] ABSTRACT

A back stretching system is provided including a stationary rest. A movable rest is slidable with respect to the stationary rest in constant coplanar relationship therewith. The movable rest and stationary rest further reside in a common angled plane during use.

3 Claims, 3 Drawing Sheets

BACK STRETCHING SYSTEM

BACKGROUND OF THE INVENTION

1. Field of the Invention

The present invention relates to therapeutic apparatuses and more particularly pertains to a new back stretching system for decompressing the lumbar area of the spine to correct the condition of herniated and bulging discs by using gravity.

2. Description of the Prior Art

The use of therapeutic apparatuses is known in the prior art. More specifically, therapeutic apparatuses heretofore devised and utilized are known to consist basically of familiar, expected and obvious structural configurations, notwithstanding the myriad of designs encompassed by the crowded prior art which have been developed for the fulfillment of countless objectives and requirements.

Known prior art therapeutic apparatuses include U.S. Pat. No. 4,951,654; U.S. Pat. No. 5,131,103; U.S. Pat. No. Des. 349,344; U.S. Pat. No. 5,409,452; U.S. Pat. No. 5,067,483; and U.S. Pat. No. 4,508,109.

In these respects, the back stretching system according to the present invention substantially departs from the conventional concepts and designs of the prior art, and in so doing provides an apparatus primarily developed for the purpose of decompressing the lumbar area of the spine to correct the condition of herniated and bulging discs by using gravity.

SUMMARY OF THE INVENTION

In view of the foregoing disadvantages inherent in the known types of therapeutic apparatuses now present in the prior art, the present invention provides a new back stretching system construction wherein the same can be utilized for decompressing the lumbar area of the spine to correct the condition of herniated and bulging discs by using gravity.

The general purpose of the present invention, which will be described subsequently in greater detail, is to provide a new back stretching system apparatus and method which has many of the advantages of the therapeutic apparatuses mentioned heretofore and many novel features that result in a new back stretching system which is not anticipated, rendered obvious, suggested, or even implied by any of the prior art therapeutic apparatuses, either alone or in any combination thereof.

To attain this, the present invention generally comprises a stationary rest with a frame having a pair of elongated longitudinal members coupled in spaced parallel relationship via a lateral member. As shown in FIGS. 3 & 4, the lateral member is coupled between ends of the longitudinal members. A padded extent is provided having a planar rectangular configuration and mounted between the longitudinal members adjacent ends thereof opposite the lateral member. Next included is a flexible rectangular strap having ends removably coupled to one of a plurality of linearly aligned apertures formed in the longitudinal members of the stationary rest. Such apertures reside adjacent to one of the ends thereof opposite the lateral member. By this structure, the rectangular strap traverses a top surface of the padded extent of the stationary rest for securing legs of a user with respect to the padded extent. A stationary rest elevation mechanism includes a pair of legs. Each of such legs has a top end pivotally coupled to a bottom face of the stationary rest adjacent to the end thereof opposite the lateral member. The legs are thus adapted for pivoting between an erected orientation for supporting the stationary rest at an angled orientation and a retracted orientation for storage purposes. FIGS. 2 & 3 best show a padded movable rest having a planar configuration with a square central extent with a width greater than that of the padded extent of the stationary rest. The movable rest further has a first end with a width equal to that of the padded extent of the stationary rest and a second end with a width equal to the central extent. A cutout is centrally formed in the movable rest which has a width equal to that of the padded extent. The padded movable rest is slidably coupled between the longitudinal members of the stationary rest and adapted to slide within a plane in which the padded extent of the stationary rest resides. During use, the padded movable rest is adapted to slide between the padded extent of the stationary rest and the lateral member thereof. Also provided is an electromagnetic locking assembly including a metal plate coupled to a bottom surface of the padded extent of the stationary rest. Associated therewith is an electromagnet coupled to a bottom surface of the movable rest. The electromagnet serves for generating a magnetic field upon the actuation thereof. When actuated, the electromagnet serves for coupling with the metal plate. Mounted to the bottom surface of the movable rest adjacent to a side edge thereof is a control toggle switch. The control toggle switch has a first orientation for actuating the electromagnet and a second orientation for preventing the actuation thereof.

It is therefore an object of the present invention to provide a new back stretching system apparatus and method which has many of the advantages of the therapeutic apparatuses mentioned heretofore and many novel features that result in a new back stretching system which is not anticipated, rendered obvious, suggested, or even implied by any of the prior art therapeutic apparatuses, either alone or in any combination thereof.

It is another object of the present invention to provide a new back stretching system which may be easily and efficiently manufactured and marketed.

It is a further object of the present invention to provide a new back stretching system which is of a durable and reliable construction.

An even further object of the present invention is to provide a new back stretching system which is susceptible of a low cost of manufacture with regard to both materials and labor, and which accordingly is then susceptible of low prices of sale to the consuming public, thereby making such back stretching system economically available to the buying public.

Still yet another object of the present invention is to provide a new back stretching system which provides in the apparatuses and methods of the prior art some of the advantages thereof, while simultaneously overcoming some of the disadvantages normally associated therewith.

Still another object of the present invention is to provide a new back stretching system for decompressing the lumbar area of the spine to correct the condition of herniated and bulging discs by using gravity.

Even still another object of the present invention is to provide a new back stretching system that includes a stationary rest. A movable rest is slidable with respect to the stationary rest in constant coplanar relationship therewith. The movable rest and stationary rest further reside in a common angled plane during use.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
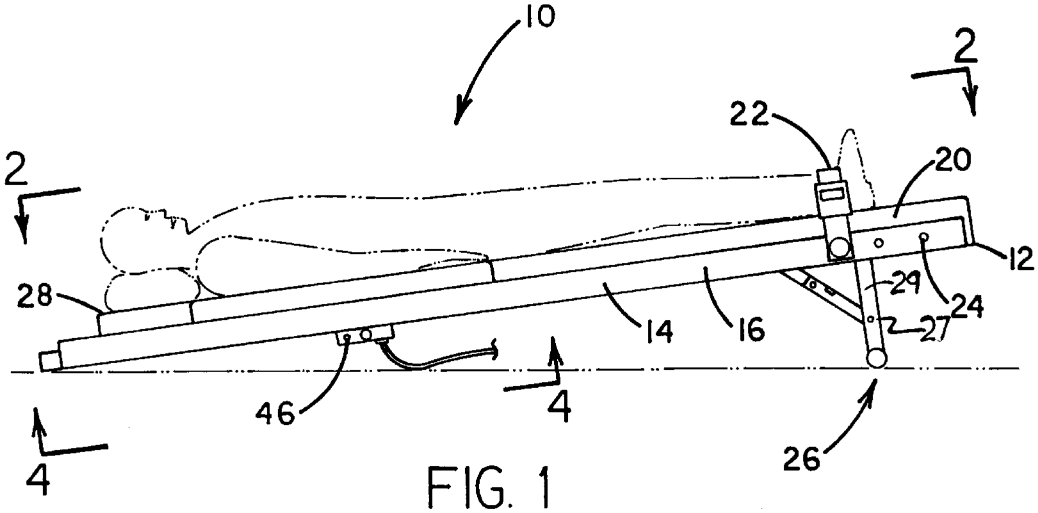
FIG. 1 is a side view of a new back stretching system according to the present invention.

With reference now to the drawings, and in particular to FIGS. 1 through 6 thereof, a new back stretching system embodying the principles and concepts of the present invention and generally designated by the reference numeral 10 will be described.

Figure 3:
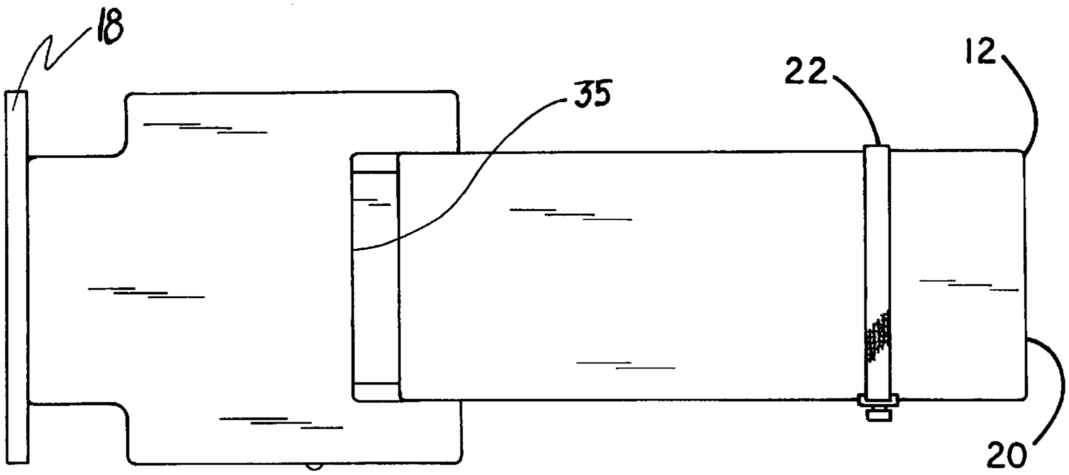
FIG. 3 is a top view of the present invention with the stationary and movable rest spaced apart.
Figure 4:
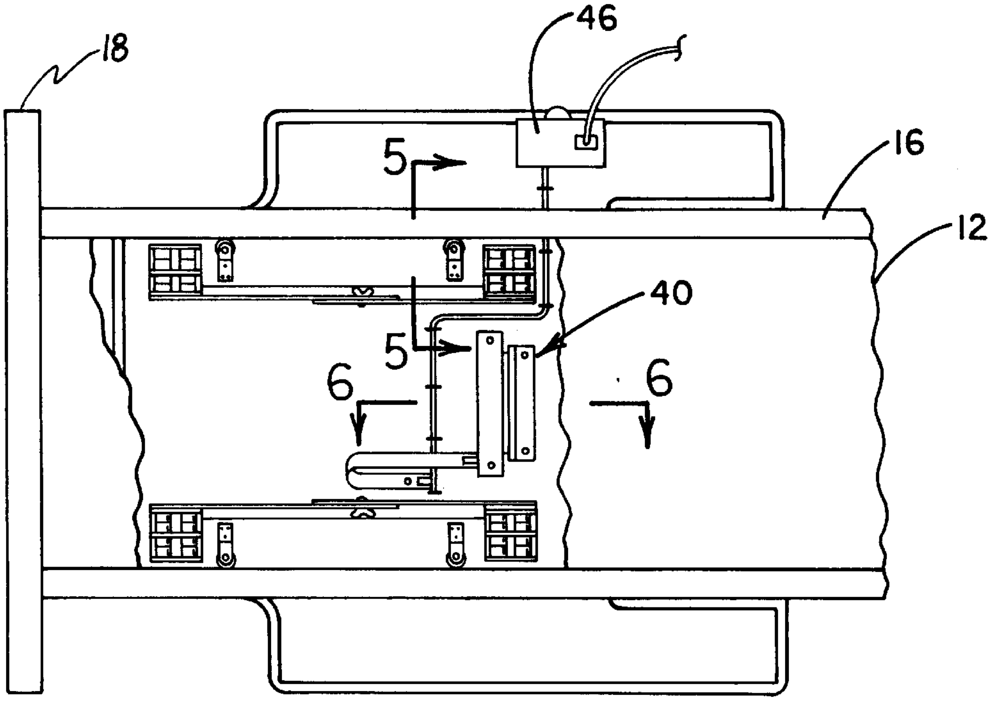
FIG. 4 is a bottom view of the present invention.
Figure 5:
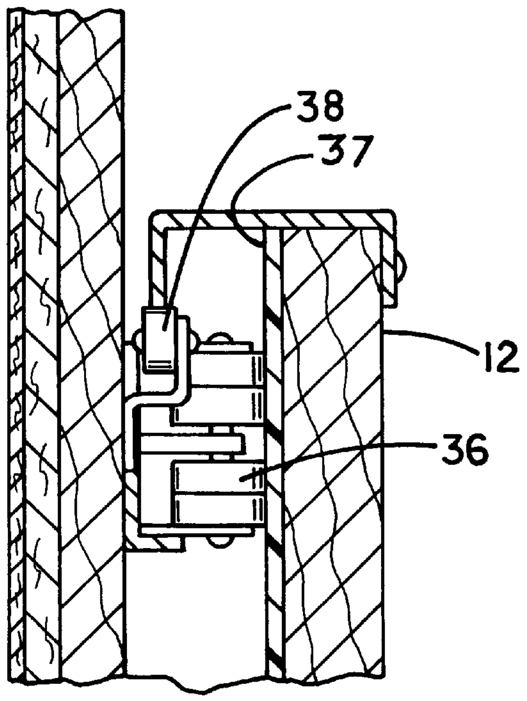
FIG. 5 is a cross-sectional view of the present invention taken along line 5—5 shown in FIG. 4.
Figure 6:
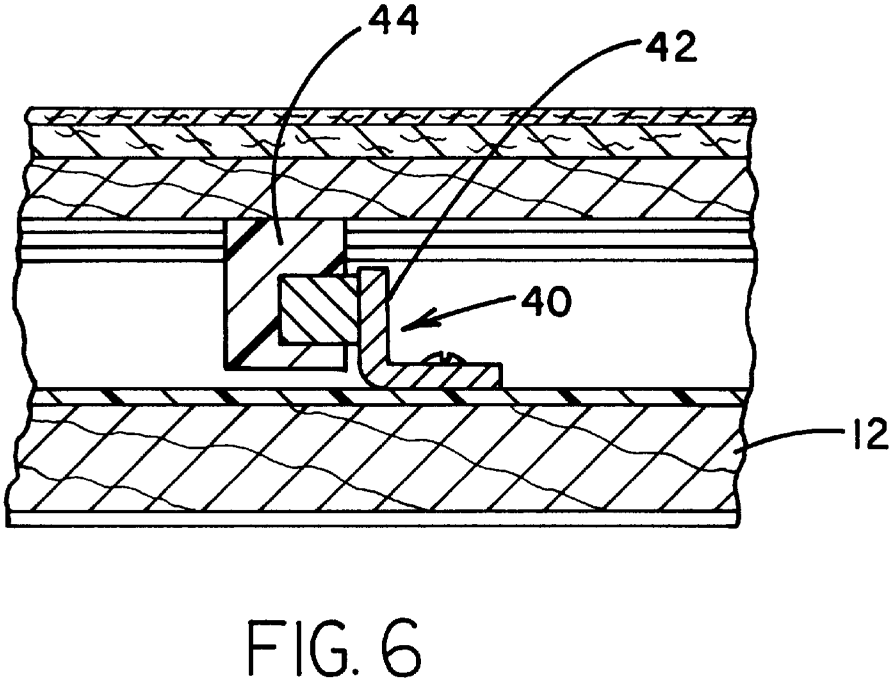
FIG. 6 is a cross-sectional view of the present invention taken along line 6—6 shown in FIG. 4.

The present invention, designated as numeral 10, includes a stationary rest 12 with a frame 14 having a pair of elongated longitudinal members 16 coupled in spaced parallel relationship via a lateral member 18. As shown in FIGS. 3 & 4, the lateral member is coupled between ends of the longitudinal members. A padded extent 20 is provided having a planar rectangular configuration. The padded extent is mounted between the longitudinal members' adjacent ends thereof opposite the lateral member. The padded extent has a length that constitutes about ½ the length of the entire stationary rest.

Next included is a flexible rectangular strap 22 having ends removably coupled to one of a plurality of linearly aligned apertures 24 formed in the longitudinal members of the stationary rest. Such apertures reside adjacent to one of the ends of the longitudinal members opposite the lateral member. Pins or the like may be employed to accomplish the coupling of the strap with the apertures. By this structure, the rectangular strap traverses a top surface of the padded extent of the stationary rest for securing legs of a user with respect to the padded extent. As an option, the strap may be equipped with a buckle for selectively adjusting its length.

A stationary rest elevation mechanism 26 includes a pair of legs 27. Each of such legs has a top end pivotally coupled to a bottom face of the stationary rest adjacent to the end thereof opposite the lateral member. The legs are thus adapted for pivoting between an erected orientation for supporting the stationary rest at an angled orientation and a retracted orientation for storage purposes. Preferably, the legs have an adjustable length for allowing the selective determination of the angle of the stationary rest. As shown in FIG. 1, a pair of adjustable supports 29 may be pivotally coupled between the legs and the padded extent of the stationary rest for only allowing the pivoting of the legs about 90 degrees.

Figure 2:
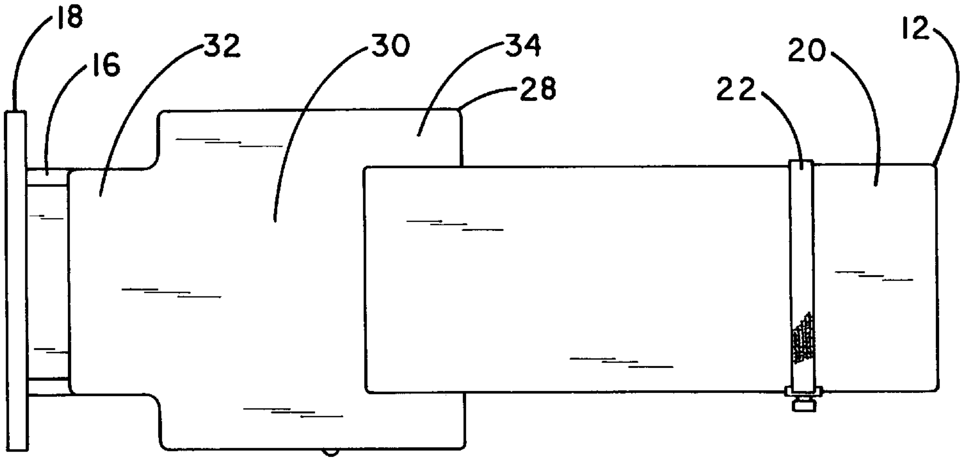
FIG. 2 is a top view of the present invention with the stationary and movable rest in abutment.

FIGS. 2 & 3 best show a padded movable rest 28 having a planar configuration with a square central extent 30 with a width greater than that of the padded extent of the stationary rest. The movable rest further has a first end 32 with a width equal to that of the padded extent of the stationary rest and a second end 34 with a width equal to the central extent. A cutout 35 is centrally formed in the second end of movable rest, wherein the cutout has a width equal to that of the padded extent. By this design, a pair of arm rests are defined for reasons that will become apparent hereinafter.

The padded movable rest is slidably coupled between the longitudinal members of the stationary rest and adapted to slide within a plane in which the padded extent of the stationary rest resides. During use, the padded movable rest is adapted to slide between the padded extent of the stationary rest and the lateral member thereof. To accomplish the sliding nature of the movable rest, the longitudinal members have a rigid roller plate 37 mounted therebetween with the longitudinal bars extending thereabove. Note FIG. 5. The movable rest is equipped with a plurality of primary rollers 36 rotatable about a horizontal axis mounted thereon and movable along a top surface of the roller plate. Further, a plurality of secondary rollers 38 rotatable about a vertical axis are movable along the longitudinal members.

Also provided is an electromagnetic locking assembly 40 including a metal plate 42 coupled to a bottom surface of the padded extent of the stationary rest. Associated therewith is an electromagnet 44 coupled to a bottom surface of the movable rest. The electromagnet serves for generating a magnetic field upon the actuation thereof. When actuated, the electromagnet is adapted for coupling with the metal plate.

Mounted to the bottom surface of the movable rest adjacent to a side edge thereof is a control toggle switch 46. The control toggle switch has a first orientation for actuating the electromagnet and a second orientation for preventing the actuation thereof.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A back stretching system comprising, in combination:

a stationary rest including a frame having a pair of elongated longitudinal members coupled in spaced parallel relationship via a lateral member coupled between ends of the longitudinal members and a padded extent having a planar rectangular configuration mounted between the longitudinal members adjacent ends thereof opposite the lateral member;

a flexible rectangular strap having ends removably coupled to one of a plurality of linearly aligned apertures formed in the longitudinal members of the stationary rest adjacent to one of the ends thereof opposite the lateral member, whereby the rectangular strap traverses a top surface of the padded extent of the stationary rest for securing legs of a user with respect to the padded extent;

a stationary rest elevation mechanism including a pair of legs each having a top end pivotally coupled to a bottom face thereof adjacent to the end thereof opposite the lateral member for pivoting between an erected orientation for supporting the stationary rest at an angled orientation and a retracted orientation for storage purposes;

a padded movable rest having a planar configuration with a square central extent with a width greater than that of the padded extent of the stationary rest, a first end with a width equal to that of the padded extent of the stationary rest, and a second end with a width equal to the central extent and a cutout formed therein which has a width equal to that of the padded extent, the padded movable rest slidably coupled between the longitudinal members of the stationary rest and adapted to slide within a plane in which the padded extent of the stationary rest resides between the padded extent of the stationary rest and the lateral member thereof;

an electromagnetic locking assembly including a metal plate coupled to a bottom surface of the padded extent of the stationary rest and an electromagnet coupled to a bottom surface of the movable rest for generating a magnetic field upon the actuation thereof for coupling with the metal plate; and a control toggle switch mounted to the bottom surface of the movable rest adjacent to a side edge of the central extent thereof, the control toggle switch having a first orientation for actuating the electromagnet and a second orientation for preventing the actuation thereof.

2. A back stretching system comprising:

a stationary rest including a frame having a pair of elongated longitudinal members coupled in spaced parallel relationship via a lateral member coupled between ends of the longitudinal members and a first extent mounted between the longitudinal members adjacent ends thereof opposite the lateral member;

a movable rest slidably coupled to the stationary rest in constant coplanar relationship therewith, wherein the movable rest and stationary rest reside in a common angled plane, the movable rest having a substantially planar configuration with a central second extent with a width greater than that of the first extent of the stationary rest, a first end with a width equal to that of the first extent of the stationary rest, and a second end with a width equal to the central second extent and a cutout formed therein which has a width equal to that of the first extent, the movable rest slidably coupled between the longitudinal members of the stationary rest and adapted to slide within a plane in which the first extent of the stationary rest resides between the first extent of the stationary rest and the lateral member thereof;

a plurality of first rollers rotatably mounted to the movable rest about horizontal axes for rolling on the stationary rest;

a plurality of second rollers rotatably mounted to the movable rest about vertical axes for rolling along the longitudinal members on the stationary rest for constraining lateral movement thereof;

a strap for fixing feet of a user with respect to the stationary rest, the strap having ends coupled to one of a plurality of linearly aligned apertures formed in the longitudinal members of the stationary rest adjacent to one of the ends thereof opposite the lateral member, whereby the strap traverses a top surface of the first extent of the stationary rest for securing legs of a user with respect to the first extent;

an electromagnetic locking assembly including a plate coupled to a bottom surface of the first extent of the stationary rest and an electromagnet coupled to a bottom surface of the movable rest for generating a magnetic field upon the actuation thereof for coupling with the plate; and a switch mounted to the bottom surface of the movable rest adjacent to a side edge of the central second extent thereof, the switch having a first orientation for actuating the electromagnet and a second orientation for preventing the actuation thereof;

wherein the stationary rest has a pair of legs for maintaining the same in the angled plane.

3. A back stretching system as set forth in claim 2 wherein the legs are collapsible.

* * * * *